United States Patent [19]

Dreikorn et al.

[11] 4,008,322

[45] Feb. 15, 1977

[54] TRIAZOLO(4,3-A)QUINOXALINES FOR CONTROL OF RICE

[75] Inventors: Barry A. Dreikorn; Thomas D. Thibault, both of Indianapolis, Ind.

[73] Assignee: Eli Lilly and Company, Indianapolis, Ind.

[22] Filed: June 10, 1975

[21] Appl. No.: 585,534

[52] U.S. Cl. .............................. 424/250; 260/250 Q
[51] Int. Cl.² ............................................ A01N 9/22
[58] Field of Search ................................... 424/250

[56] References Cited

UNITED STATES PATENTS 3,764,681  10/1973  Dreikorn ........................... 424/258

FOREIGN PATENTS OR APPLICATIONS 803,098  3/1973  Belgium

OTHER PUBLICATIONS

Shiho et al., J. Am. Chem. Soc., 82, (1960), pp. 4044–4054.

*Primary Examiner*—V. D. Turner
*Attorney, Agent, or Firm*—Joseph A. Jones; Everet F. Smith

[57] ABSTRACT

A new method of reducing the adverse effects of rice blast, an important disease of rice, is disclosed. The method comprises applying a compound chosen from a class of triazolo[4,3-a]quinoxalines to the foliage of the rice plants.

6 Claims, No Drawings

TRIAZOLO(4,3-A)QUINOXALINES FOR CONTROL OF RICE

BACKGROUND OF THE INVENTION

For many years, rice has been the mainstay of life for a large proportion of the world's population. Since the crop is necessarily grown in moist, tropical climates, it is necessary to protect the crop against phytopathogens in order to obtain a satisfactory yield. One of the most important phytopathogens which afflicts rice is *Piricularia oryzae*, the causative organism of rice blast.

This invention provides a new method of reducing the adverse effects of rice blast.

A few prior publications are important to the understanding of the background of this invention. U.S. Pat. Nos. 3,764,681 and 3,839,569 disclosed the fungicidal efficacy of tetrazolo[1,5-a]quinolines and s-triazolo-[4,3-a]quinolines, respectively. Belgian Pat. No. 803,098 and West German Offenlegungsschrift No. 2,249,350 disclosed that certain imidazoquinoxalines were also useful as agricultural fungicides.

SUMMARY OF THE INVENTION

The invention described here is a new method of reducing the adverse effects of rice blast which comprises contacting the causative phytopathogen, *Piricularia oryzae*, on the foliage of rice plants with a compound of the formula

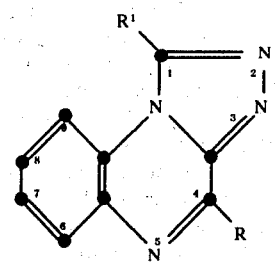

wherein
R represents chloro, amino, hydrazino or hydrogen;
R reaction mixture was then cooled, and was evaporated to dryness under vacuum. The product was found to melt at 210°–12° C. without purification, and was identified as 1-methyl-s-triazolo[4,3-a]quinoxaline by NMR analysis and elemental microanalysis, the results of which follow.

|   | Theoretical | Found |
|---|---|---|
| C | 65.21% | 64.95% |
| H | 4.38 | 4.35 |
| N | 30.42 | 30.31 |

The compounds described above have been shown in in vivo tests to protect rice plants from the adverse effects of P. oryzae, which causes the damaging disease rice blast. The tests employed and the results produced by representative compounds will be described.

Each compound was formulated for testing by dissolving or suspending about 3.5 weight percent of it in 50:50 acetone-ethanol containing about 10 g./100 ml. of a nonionic surfactant. The solution was then dispersed in deionized water in a quantity such that the water dispersion contained the various compound concentrations indicated in the table below. Concentrations are measured in parts per million by weight.

The compound dispersions were applied to the test plants by spraying them with an air atomizer, using sufficient dispersion to wet the plants thoroughly.

Untreated, infected controls and untreated, normal controls were included in each test. The results are reported on a 1–5 rating scale where 1 indicates severe disease and 5 indicates complete control of the disease. An empty space in the tables below shows that the indicated compound was not tested at the indicated rate. In some cases, more than one test was performed at a given rate and the results in such cases are reported as averages.

The test compound dispersions, at compound concentrations indicated in the table below, were applied to healthy rice seedlings growing thickly in plastic pots. The plants were inoculated on the next day by spraying the foliage with a conidial suspension of *P. oryzae* (grown on rice polish agar) and the plants were held in a moist chamber for 2 days. The plants were then held in the greenhouse for 5–7 days and observed.

The table below reports results of testing typical compounds of the invention against *P. oryzae*.

| Compound | Appln. Rate ppm. | Rice Blast |
|---|---|---|
| s-triazolo[4,3-a]-quinoxaline | 400 | 4.6 |
| | 80 | 3.5 |
| | 16 | 1.5 |
| | 3.2 | 1 |
| 4-chloro-s-triazolo-[4,3-a]quinoxaline | 400 | 3.6 |
| | 80 | 1 |
| | 16 | 1 |
| 4-hydrazino-s-triazolo-[4,3-a]quinoxaline | 400 | 3 |
| 1-methyl-s-triazolo-[4,3-a]quinoxaline | 400 | 4 |
| | 80 | 2 |
| | 16 | 1 |

Many of the compounds of this method are also useful for the control of other phytopathogens, as well as for protection of rice against rice blast. For example, s-triazolo[4,3-a]quinoxaline and 4-chloro-s-triazolo[4,3-a]-quinoxaline are useful for the control of anthracnose disease of cucumber. Crown gall of tomato is controlled by 1-methyl-s-triazolo[4,3-a]quinoxaline, and late blight is controlled by s-triazolo[4,3-a]quinoxaline, 4-chloro-s-triazolo[4,3-a]quinoxaline, and 4-hydrazino-s-triazolo[4,3-a]quinoxaline.

This invention is a method of reducing the adverse effects of rice blast which comprises contacting the causative phytopathogen, *P. oryzae*, with an effective Piricularia-inhibiting amount of one of the compounds described above. The method is carried out by applying the compound to the foliage of rice.

Practice of the method does not necessarily kill the contacted phytopathogens. As the data above show, application of a sufficient amount of a compound of the invention to inhibit the phytopathogen reduces the adverse effects of the disease, even if only a part of the pathogen population is killed by the compound.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the plants to be protected, are entirely conventional in the plant protection art. Some explanation of the methods of application will be given merely to assure that those skilled in the art can carry out the invention without undue experimentation.

It is usual in describing foliar applications of plant protectants to measure the application rate by the concentration of the dispersion in which it is applied. The application rate is measured in this way because it is customary to apply a sufficient amount of the dispersion to cover the foliage with a thin film. The amount of dispersion applied is thus dependent on the foliar area of the plants being treated, and the quantity of plant protecting compound is dependent upon its concentration in the dispersion.

Compound concentrations in the range of from about 25 to about 1500 parts of compound per million parts by weight of the dispersion are used in the practice of this invention. Of course, from time to time, higher or lower concentrations will be useful, depending on the severity of the infection and the characteristics of the specific compound in use. The named range, however, encloses the usual optimum concentrations of the compounds.

The dispersions in which the compounds are applied to foliage are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

Adjuvants are frequently used to improve the ability of the aqueous dispersion to coat and adhere to foliage. Such adjuvants as gums, emulsified polybutenes, cationic surfactants and lignin derivatives can often increase the potency of the method in a specific use.

Less frequently, the compounds are applied in the form of dusts. Agricultural chemical dusts typically comprise the compound in a finely powdered form, dispersed in a powdered inert carrier. Most often, the carrier is a powdered clay, such as pyrophyllite, bentonite, a volcanic deposit, or montmorillonite. Dusts are usually prepared to contain concentrations of the compound at the highest part of the concentration range, such as 1500 ppm., and may contain even more active ingredient.

Dispersions of the compounds are applied to foliage in the usual manners. Low-pressure sprayers, high-pressure sprayers and low-volume air blast equipment are all effective for the application of water-dispersed compounds of the invention. Dust dispersions are readily applied by means of the usual equipment which blows the dust into intimate contact with the foliage.

We claim:

1. A method of reducing the adverse effects of rice blast which comprises contacting *Piricularia oryzae* on the foliage of rice with an effective Piricularia-inhibiting amount of a compound of the formula wherein
R represents chloro, amino, hydrazino or hydrogen;
$R^1$ represents methyl or hydrogen; and
provided that at least one of R and $R^1$ represents hydrogen.

2. The method of claim 1 in which the compound is applied in a concentration from about 25 to about 1500 ppm.

3. The method of claim 1 in which the compound is -s-triazolo[4,3-a]quinoxaline.

4. The method of claim 1 in which the compound is 4-chloro-s-triazolo[4,3-a]quinoxaline.

5. The method of claim 1 in which the compound is 4-hydrazino-s-triazolo[4,3-a]quinoxaline.

6. The method of claim 1 in which the compound is 1-methyl-s-triazolo[4,3-a]quinoxaline.

* * * * *